(12) United States Patent
Bloecker et al.

(10) Patent No.: US 6,592,826 B1
(45) Date of Patent: Jul. 15, 2003

(54) DIFFERENTIAL VACUUM CHAMBER FOR DIRECTED TRANSPORT OF A SUBSTANCE

(75) Inventors: Helmut Bloecker, Braunschweig (DE); Gerhard Kauer, Braunschweig (DE)

(73) Assignee: Gesellschaft fuer Biotechnologische Forschung mbH (GBF), Braunschweig (DE)

( * ) Notice: Subject to any disclaimer, the term of this patent is extended or adjusted under 35 U.S.C. 154(b) by 0 days.

(21) Appl. No.: 09/446,251

(22) PCT Filed: Jun. 19, 1998

(86) PCT No.: PCT/EP98/03763

§ 371 (c)(1),
(2), (4) Date: Mar. 28, 2000

(87) PCT Pub. No.: WO98/57746

PCT Pub. Date: Dec. 23, 1998

(30) Foreign Application Priority Data

Jun. 19, 1997 (DE) .......................... 197 25 894

(51) Int. Cl.[7] .................................................. B01L 11/00
(52) U.S. Cl. ...................... 422/101; 436/174; 436/177; 436/178; 422/99; 210/224; 210/231; 210/294; 210/295
(58) Field of Search .......................... 422/58, 99, 100, 422/101, 129, 130, 131, 134; 435/283.1, 286.6, 287.7, 287.8; 210/224, 227, 231, 294, 295, 406; 95/273, 284, 286; 436/174, 177, 178

(56) References Cited

U.S. PATENT DOCUMENTS

| | | | | | |
|---|---|---|---|---|---|
| 5,380,437 A | * | 1/1995 | Bertoncini | ............... | 210/416.1 |
| 5,948,246 A | * | 9/1999 | Zuk, Jr. | ....................... | 210/160 |
| 6,054,100 A | * | 4/2000 | Stanchfield et al. | ......... | 422/102 |
| 6,117,397 A | * | 9/2000 | Antonenko et al. | .......... | 422/101 |
| 6,153,104 A | * | 11/2000 | Robertson | .................... | 210/650 |
| 6,159,368 A | * | 12/2000 | Moring et al. | ......... | 210/321.75 |
| 6,265,229 B1 | * | 7/2001 | Fodstad et al. | .............. | 436/526 |

* cited by examiner

*Primary Examiner*—Jill Warden
*Assistant Examiner*—Dwayne K Handy
(74) *Attorney, Agent, or Firm*—Frommer Lawrence & Haug; Ronald R. Santucci

(57) ABSTRACT

In a vacuum chamber, which has at least two vacuum regions, substances, especially fluids, are transported in a directed manner from one region into the other region by the application of a suitable vacuum. As a result, it is possibly by the use of filter supports or receiver supports to transport a fluid automatically through corresponding filter supports during a plasmid preparation. The vacuum chamber is charged by means of a gripping robot that operates automatically and is switched by a suitable valve control means. By incorporating the vacuum chamber with its gripping robot and the control means into a pipetting robot system, automatic plasmid preparation, for example in accordance with the Qiagen protocol, is possible.

33 Claims, 10 Drawing Sheets

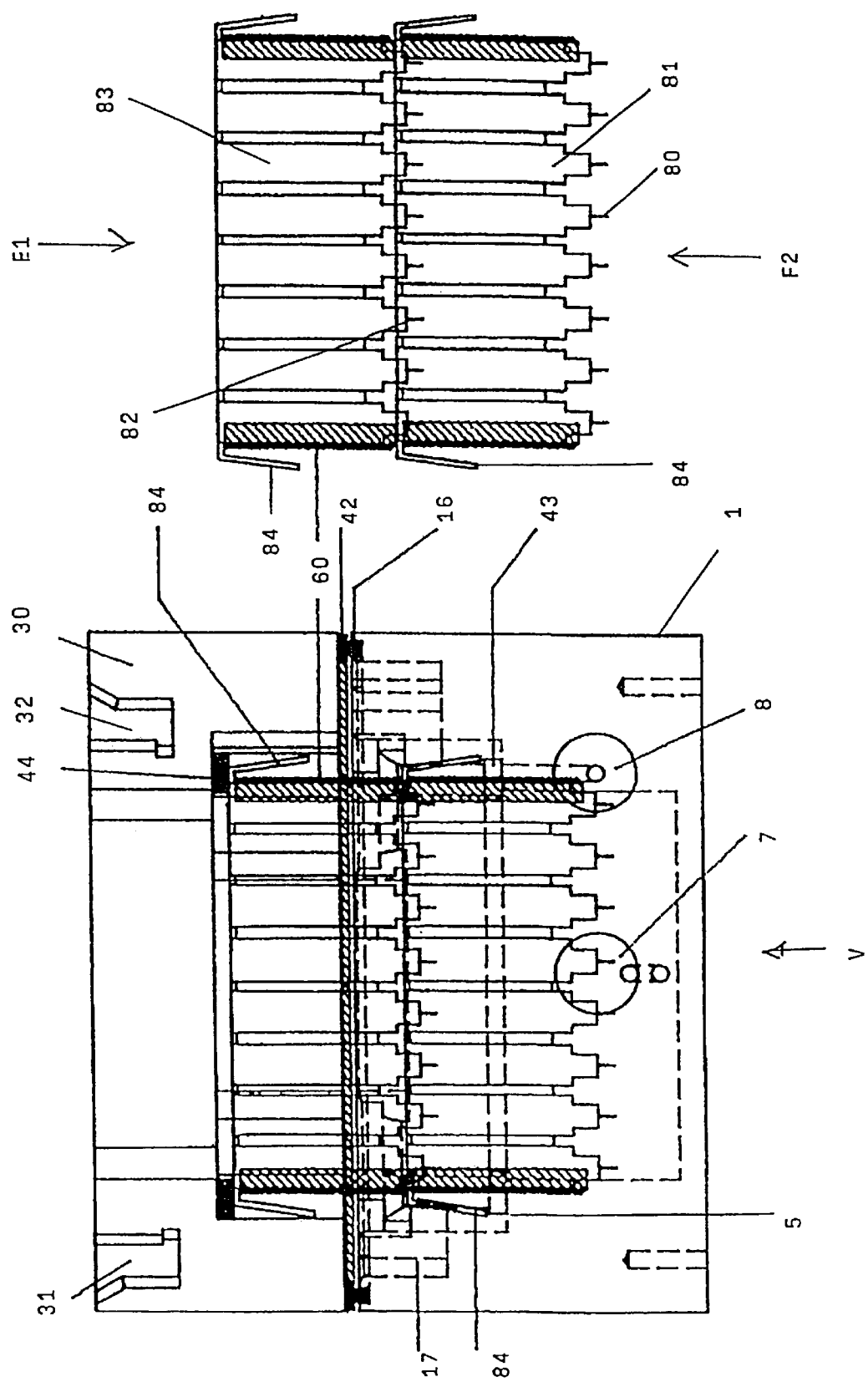

DIFFERENTIAL VACUUM CHAMBER FOR DIRECTED TRANSPORT OF A SUBSTANCE

The present invention relates to a vacuum chamber and a vacuum system using the vacuum chamber for the directed transport of a substance, especially a fluid, and to its use in an apparatus for automatic plasmid preparation.

The past few years have seen an increase in the scale of efforts to obtain the complete genetic information of entire organisms. Beginning with the sequencing of a phage genome (bacteriophage T7: 38000 base pairs, bacteriophage λ: 48514 base pairs) and continuing by way of the genome of *Escherichia coil* ($4.2 \times 10^6$ base pairs) to the yeast *Saccharomyces cerevisiae* ($2.3 \times 10^7$ base pairs) as the first representative of the eukaryotes, the number of base pairs to be sequenced has increased almost 600-fold. In the meantime, the human genotype with more than $3 \times 10^9$ base pairs has become the goal of these efforts in the "Human Genome Project". The enormous quantities of DNA to be sequenced are barely manageable by the means and personnel available to laboratories hitherto. There is therefore a demand for new technologies that, for an acceptable financial outlay, are capable of bringing about a considerable increase in the throughput of samples in this research programme. Two mutually influencing strategies have come to light in the course of current development: on the one hand the miniaturisation of laboratory sequences and on the other hand the unsupervised automation of well-established laboratory procedures.

The miniaturisation of laboratory sequences has given rise to miniaturised electrophoresis analysers in which the separation of biomolecules on the basis of their charge and size is utilised. Such miniaturised electrophoresis analysers are obtained by means of microstructures in electrophoresis chips. Also available are miniaturised PCR machines, wherein during the polymerase chain reaction (polymerase chain reaction=PCR) DNA fragments up to 6 kilobases in size are amplified. Also known are miniaturised sample arrays and miniaturised detection systems. Miniaturised elements such as those described above can be combined to form larger units, so that a complete miniaturised laboratory unit is obtained.

On the other hand, for the automation of a laboratory it is not absolutely necessary to miniaturise routine procedures. It is likewise possible to design a robot system that completely or partially replaces the manual tasks of a human being in order to achieve an increase in sample throughput. The following manual tasks are typical of a laboratory preparation (with particular emphasis on plasmid preparation as a preliminary to PCR sequencing) and need to be carried out by suitable robots:

pipetting transport of used material and of chemicals suction of fluids through filters, membranes, permeable solids or the like PCR reaction.

Current pipetting robots locate standard laboratory material on a work surface at defined positions and thus enable tested laboratory protocols to be set up. For example, using auxiliary robots it is possible for microtitre plates, pipette tips or reservoirs for buffer solutions etc. to be installed on such machines and, after use, removed from the workstation again. Thus, all the necessary pipetting steps preliminary to a PCR or a plasmid preparation can be executed in order that the product of that pipetting operation can then be introduced into a suitable machine for further preparation using a gripping robot.

The polymerase chain reaction (PCR) amplifies a DNA segment when it is enclosed between two defined primer sites. If equal amounts of primers are used, double-stranded DNA copies are produced by the PCR, whereas if one primer is used in excess then, in accordance with that excess, single-stranded copies of the amplified DNA are obtained. Both single-stranded and double-stranded DNA can be used for sequencing. In sequencing-intensive projects the DNA fragments to be analysed are cloned into plasmids which are then in the first instance present in a defined matrix of bacterial colonies (Escherichia Coli Blue) growing on agar. The subsequent taking up of the colonies from the matrix into culture tubes can also be automated. Over an incubation period (37° C.) lasting about 12 hours the living bacterial clones then yield sufficient material to obtain in a preparation the plasmid copies necessary for sequencing. Obtaining such purified plasmids for sequencing is achieved, for example, by the QIAWELL 96 ultraplasmid purification procedure. Such plasmid preparation procedures include filtering operations in which a fluid has to be transported in a directed manner from one filter into at least one second filter and either also passes through that filter or is simply collected in a controlled manner.

The problem underlying the invention is therefore to provide an apparatus in which the directed movement of substances can be carried out automatically.

The present invention relates to a vacuum chamber for the directed transport of a substance, especially a fluid, there being installed in the vacuum chamber a permeable means and a collecting means, so that there are defined at least two vacuum regions that can be established independently of one another, namely a first vacuum region between the permeable means and the collecting means and a second vacuum region between the collecting means and the base of the vacuum chamber, and a vacuum can be generated in the two vacuum regions independently of one another so that the substance, especially the fluid, can be sucked from the first permeable means into the collecting means. Fluids are here to be understood as being gases, liquids, vapours and fumes.

The second means is preferably also permeable, so that by the application of a vacuum to the second region the fluid or liquid is sucked through the second means into the second region. The vacuum chamber according to the invention will generally have exactly two vacuum regions, but more than two vacuum regions are possible, for example when several filtrations are to be carried out one immediately after another.

Furthermore, the permeable means are formed by filter supports having a large number of filter elements, so that fluid can be transported in a defined manner from a particular filter element of the first filter support into a corresponding filter element of the second filter support in turn through the latter into the second lower region of the vacuum chamber. The collecting means are likewise collector supports having a defined number of collecting elements. In the case of a collector support, therefore, the substance, especially the fluid, is transported through the first filter support into the collector support.

Moreover, the vacuum chamber consists of a cover and a lower part, the lower part of the vacuum chamber having a shoulder for receiving the lower filter support. In addition, recesses for the gripper of the robot are provided in the side walls of the chamber in order that the filter plates or filter supports can be inserted and removed automatically. For the exact receiving and guidance of the filter supports or the collector support the lower part of the vacuum chamber has guide tabs having correcting bevels. The guide tabs preferably have two different bevel angles, the first bevel angle being about 30° and the second bevel angle being about from 0° to 2°. Furthermore, the guide edges of the wall with which the filter supports come into contact on insertion can be bevelled. Preferably the cover has a bevelled guide edge so that when the cover is put in place it is centred using the guide edge of the cover. The edge bevel angle is preferably 30°. The cover also has in the wall region recesses for the robot gripper and a supporting surface for the upper filter support.

The sealing material for the upper filter holder preferably has a hardness of about 20 Shore, the seal at the join between the cover and the lower part being formed by a combination of an O-ring and a resilient sealing strip, the O-ring providing a seal of about 60 Shore and the sealing strip of about 30 Shore. Sealing is also effected at the lower filter support using a rubber gasket having a hardness of 60 Shore.

The upper part has corresponding receiving means for receiving the guide tabs so that the cover is centred on the lower part by means of the guide tabs.

In a preferred embodiment, the filter supports have N pipe-shaped individual filters (N being especially 96) that are connected to form a filter support. The same applies to the collector support. In addition, there are mounted on the corresponding four corner pies of the two filter supports, or of the filter support and the collector support, spacer sleeves which, in addition to their function of defining the first vacuum region, also effect the vertical correction of misplacements of the lower filter support by engaging in centring shafts in the vacuum lower part. The spacer sleeves preferably have a partially cylindrical shape in order to allow the vacuum to act on the corner pies. In addition, the spacer sleeves can be bevelled so that an additional centring of the filter supports is achieved during insertion. A filter support may be in one piece consisting of a large number of filter elements or it may be composed of a large number of individual filter elements.

The length of the spacer sleeves is preferably so selected that the outlet tips of the upper filter support are located inside the pipes of the lower filter support or collector support, so that a controlled transport of the fluid through pipes or elements that correspond to one another is achieved. The outlet tips of the elements of the upper filter support are preferably located 1.5 mm inside the corresponding pipes of the filter elements or collecting elements of the corresponding lower support. As a result, contamination of non-corresponding elements is avoided.

Preferably the vacuum chamber and the spacer sleeves are manufactured from plexiglass of a suitable thickness, which allows visual monitoring. For industrial production, the vacuum chamber may consist of a cast plastics material, which allows economical manufacture. Injection-moulding processes and milling processes may also be used.

In the lower part of the vacuum chamber there are arranged a suction shaft for the first vacuum region and a suction shaft for the second vacuum region. Fluid passing through during a filtration procedure is removed directly from the vacuum chamber through the suction shaft of the second vacuum region.

The present invention relates also to a vacuum system having at least one vacuum pump and an electronically controlled valve for the lower chamber region, an electronically controlled valve for the middle chamber region, a valve for breaking the creeping vacuum in the lower chamber region and a vacuum trap arranged between the valves and the connection to the lower region of the vacuum chamber for receiving the waste volume. Each proportional valve may have its own controlling electronics system which can be actuated by the control software via a decoding apparatus of a PC.

The invention relates also to an apparatus for automatic plasmid preparation having a vacuum system for automating the directed transport of a substance, a pipetting robot and a gripping robot, wherein the gripping robot inserts the filter supports, after pipetting has been carried out by the pipetting robot, into the vacuum chamber and closes the cover and, after filtering, opens the chamber and removes the filter supports and conveys them to a further processing step. Such an apparatus is preferably controlled by a computer. It is also possible to work with only one robot which assumes the gripping and the pipetting functions.

The apparatus also has a dryer for filter supports, because in some preparation procedures the last preparation step is washing with alcohol, so that residual alcohol adhering to the last support has to be removed.

Advantageously the vacuum chamber is part of a larger robot system which can be used for supporting all current preparation methods of molecular biology processes. A modular design has therefore been created which enables the apparatus components of the apparatus for automatic preparation to be arranged to suit the particular problem being posed. Furthermore, the robot system used has no feedback, which means that no visual or other sensory monitoring of the current actual state is possible. All the movable components of the system must therefore be located in positions that are defined as exactly as possible. When components are moved by a robot arm, it is important that those moved components, when taken up by the robot again, are located at exactly defined positions. The vacuum chamber is, in addition, removable from the system as a module so that other modular systems for other methods can be inserted in its place. Therefore the position of all auxiliary systems for the automated preparation is oriented on the pipetting robot. In order, therefore, to be able to monitor the current position of the gripping robot visually during the "learning phase" of the system, the vacuum chamber is advantageously manufactured from plexiglass or some other transparent plastics material. It is readily possible, however, to use a feedback robot system in which the feedback is provided by sensors.

By the use of the vacuum it is possible to transport fluid, in two steps well defined in time, from one filter into, for example, a second filter arranged below the first in order to be sucked through the second filter into the lowermost region and disposed of.

The invention, especially the vacuum chamber with its at least two vacuum regions which are independent of one another, is not, however, restricted to the transport of fluid in the filtering phase of a plasmid preparation. Other possible uses are the separation of mixtures, the initiation of reactions, the establishment of adsorption processes by the automation (expressed in general terms) of the directed transport of a substance by the provision of at least two vacuum regions that can be established independently of one another. "Substance" is here to be understood as a single substance or a mixture of substances in the form of a fluid, gas or fumes. Furthermore, not only filter supports can be used as the permeable means but the use of, for example, an array of miniaturised chromatography columns is likewise possible, so that time-resolved transport of a substance can also be achieved.

Preferred embodiments of the invention are explained below with reference to the drawings.

FIG. 8 shows a cross-section through the vacuum chamber with the filter supports inserted and the cover in place;

Figure 1:
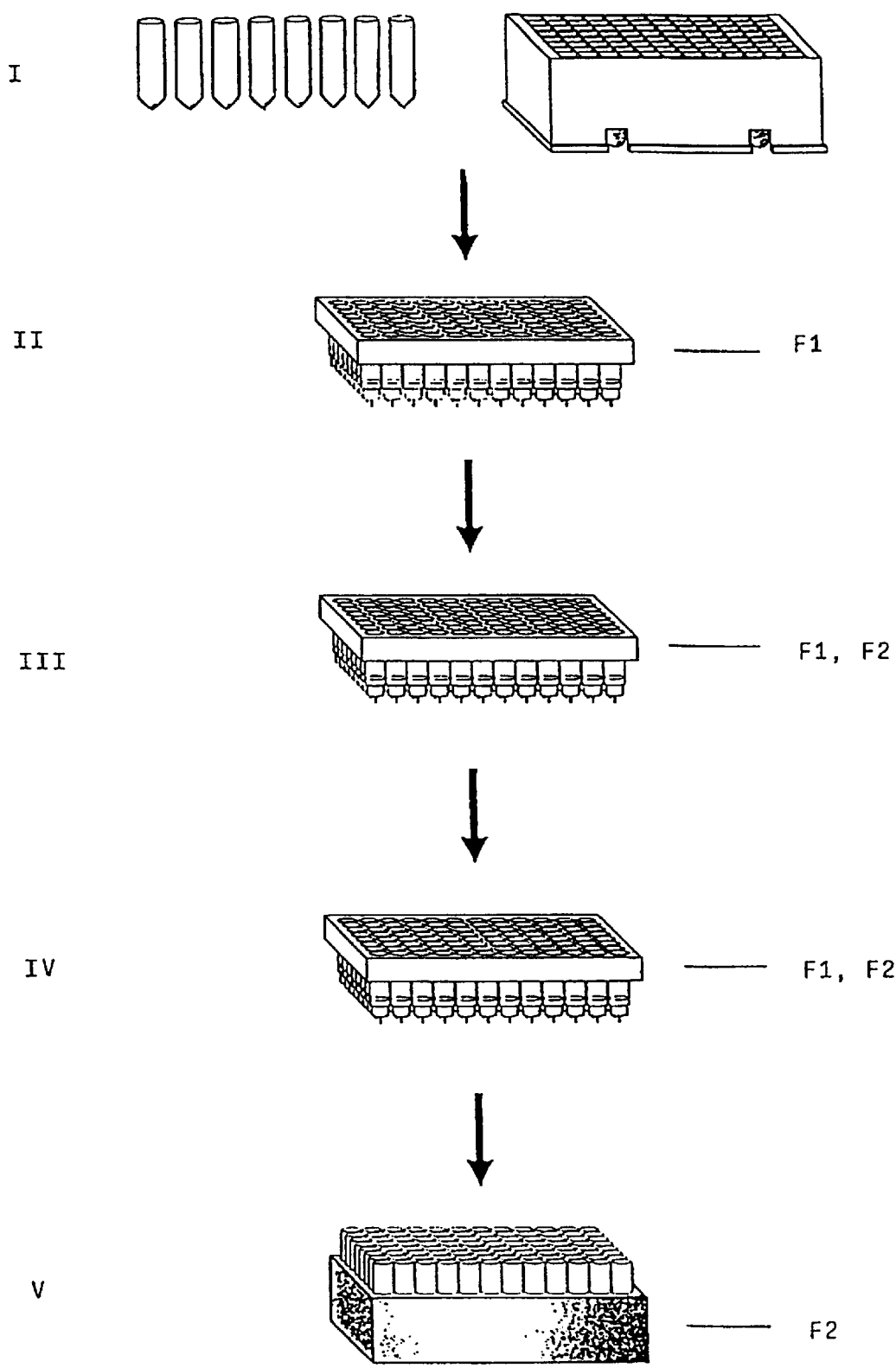
FIG. 1 is a diagram showing the course of a plasmid purification procedure in accordance with a protocol of the Qiagen company.

FIG. 1 is a diagram showing the course of a plasmid preparation or purification, as used, for example, by the Qiagen company. In Step 1 the DNA fragments to be analysed are cloned into plasmids which are then in the first instance present in a defined matrix of bacterial colonies (Escherichia Coli Blue) growing on agar. Over an incubation period at 37° C. lasting about 12 hours the living bacterial clones then yield sufficient material which is purified in accordance with the following scheme. The pellets obtained after centrifugation are resuspended in the test tubes in Step I and lysed. In Step II the samples are each pipetted into a filter element of a filter support (QIAfilter 96 (yellow)). In the filter support of Step II, the cell walls etc. are retained in the filter, while the DNA strands are flushed with the fluid into the corresponding pipes of the next filter support in Step III. In the filter elements of that second filter support (QIAWell 96 (white)) of Step III, the DNA is adsorbed on the filters, while the filter fluid flows downwards. Using a buffer fluid, the DNA on the filter elements of the second filter support is washed and conveyed using an elution buffer into a third filter support (QIAprep 96 (blue)) in Step IV. From there the DNA or the plasmids are eluted into a support consisting of collecting elements in Step V. Those plasmids collected in the individual test tubes can be conveyed to a PCR machine (not shown) in order on the one hand to increase the number of copies of the DNA and/or on the other hand to carry out a PCR sequencing step.

Figure 2:
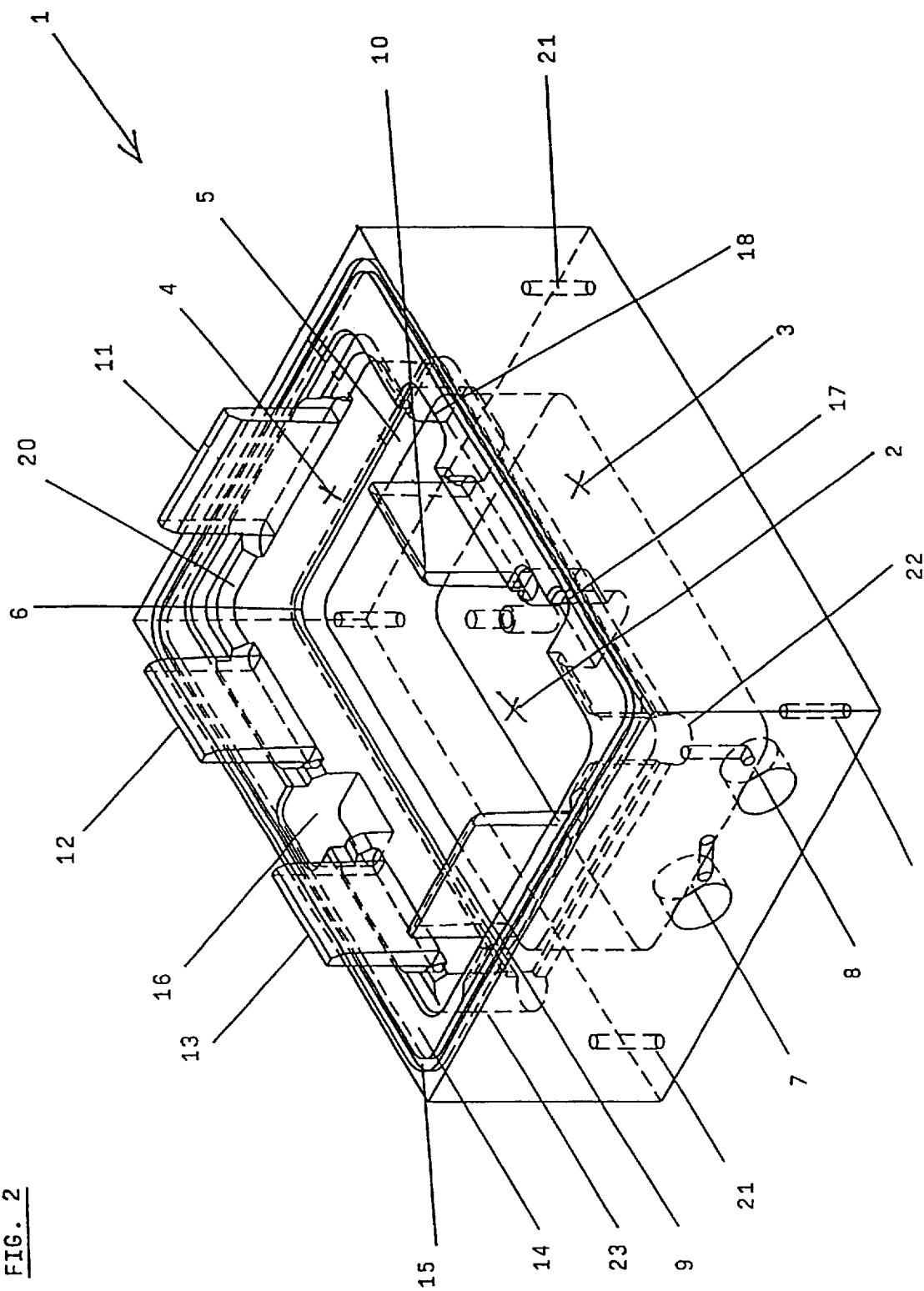
FIG. 2 shows a perspective view of the lower part of the vacuum chamber.

FIG. 2 shows a perspective view of the lower part 1 of a vacuum chamber V which is used to transport fluid from an upper filter support (not shown) into a lower filter support (not shown) or collector support (not shown), By this means the various filtration steps II to V of the plasmid purification procedure, for example in accordance with the Qiagen protocol of FIG. 1, are able to take place automatically, for example using a robot, the fluids being sucked by means of a partial vacuum from an upper filter support into or through a lower filter support.

The lower part 1 of the vacuum chamber V comprises an inner chamber 2 which is divided into a chamber base portion 3 and an upper portion 4, the division being made by a peripheral ledge 5 on which the lower filter support or receiver support is arranged. As a result of this ledge 5, the cross-section of the chamber base portion 3 is slightly smaller than that of the upper portion 4. A groove 6 has been made by means of milling along the ledge 5 on the wall side, the significance of which groove will be explained below. The lower part 1 has suction shafts 7, 8, the suction shaft 7 serving to aspirate the lower chamber base region 3, while the suction shaft 8 generates a vacuum in the upper vacuum region between the upper and lower filter supports. For the accurate positioning of the filter supports F1, F2 in the vacuum chamber V there are provided in the upper region of the lower part 1 guide tabs 9, 10, 11, 12 and 13 which project above the lower part 1. In addition, the upper end face 14 of the lower part 1 has a groove 15 for receiving a rubber seal 16 (not shown). The guide tabs 9 and 13 are provided with correcting bevels so that an enforced alignment of the filter support F1, F2 is effected on insertion. In order to be able to insert the filter supports F1, F2 there are provided in the lower part 1 of the vacuum chamber, in opposing side walls, grip recesses 17, 18 and 19 in which the gripping fingers of a robot hand engage. The lower part 1 also has on the guide edges of the chamber correcting bevels 20 which come into contact with the filter support or with spacer sleeves affixed to the filter support. Locating bores 21 are provided for fixing the position of the vacuum chamber V in the entire system. To allow the vacuum chamber V to be used with other filter supports or other filter systems, the lower part 1 of the vacuum chamber additionally has milled-out centring shafts 22 and 23 in the corners.

Figure 3:
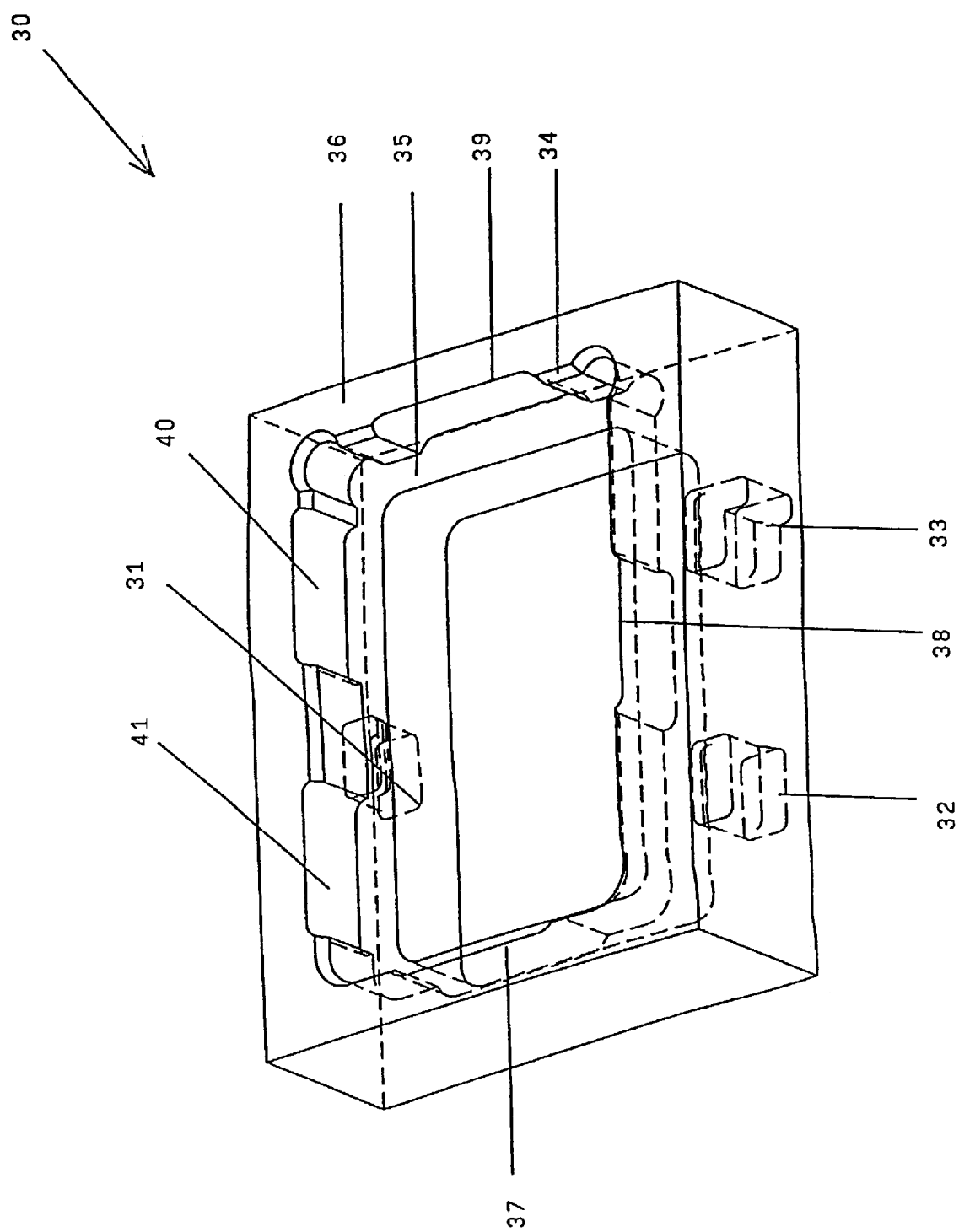
FIG. 3 shows a perspective view of the cover of the vacuum chamber.

FIG. 3 shows the cover 30 of the vacuum chamber V, viewed from below. For moving the cover 30, the cover likewise has grip recesses 31, 32 and 33 for the robot grippers. The cover also has a 30° bevel at the edge for receiving the upper filter support F1 (not shown). In the interior there is also arranged, as supporting surface for the filter support F1, a ledge 35, on which the filter support F1 is sealed by means of a suitable sealing material. The cover 30 also has a supporting surface 36 which forms the counterpart to the sealing end face 14 of the lower part 1. The cover 30 is provided with suitable recesses 37, 38, 39, 40 and 41 in which the guide tabs 9 to 13 of the lower part 1 engage when the cover 30 is put in place and effect final alignment of the cover 30. In the preferred embodiment the cover 30 is open at the top (at the bottom in FIG. 3). This is necessitated, however, by the special use of the filter supports which requires normal atmospheric pressure to be present on the upper side of the upper filter support in order for the fluid to be transported through the filter elements by the pressure differential between the external air pressure and the upper vacuum region. For other uses, where, for example, no vapour is to be allowed to escape into the environment, the cover 30 may be closed.

Figure 4:
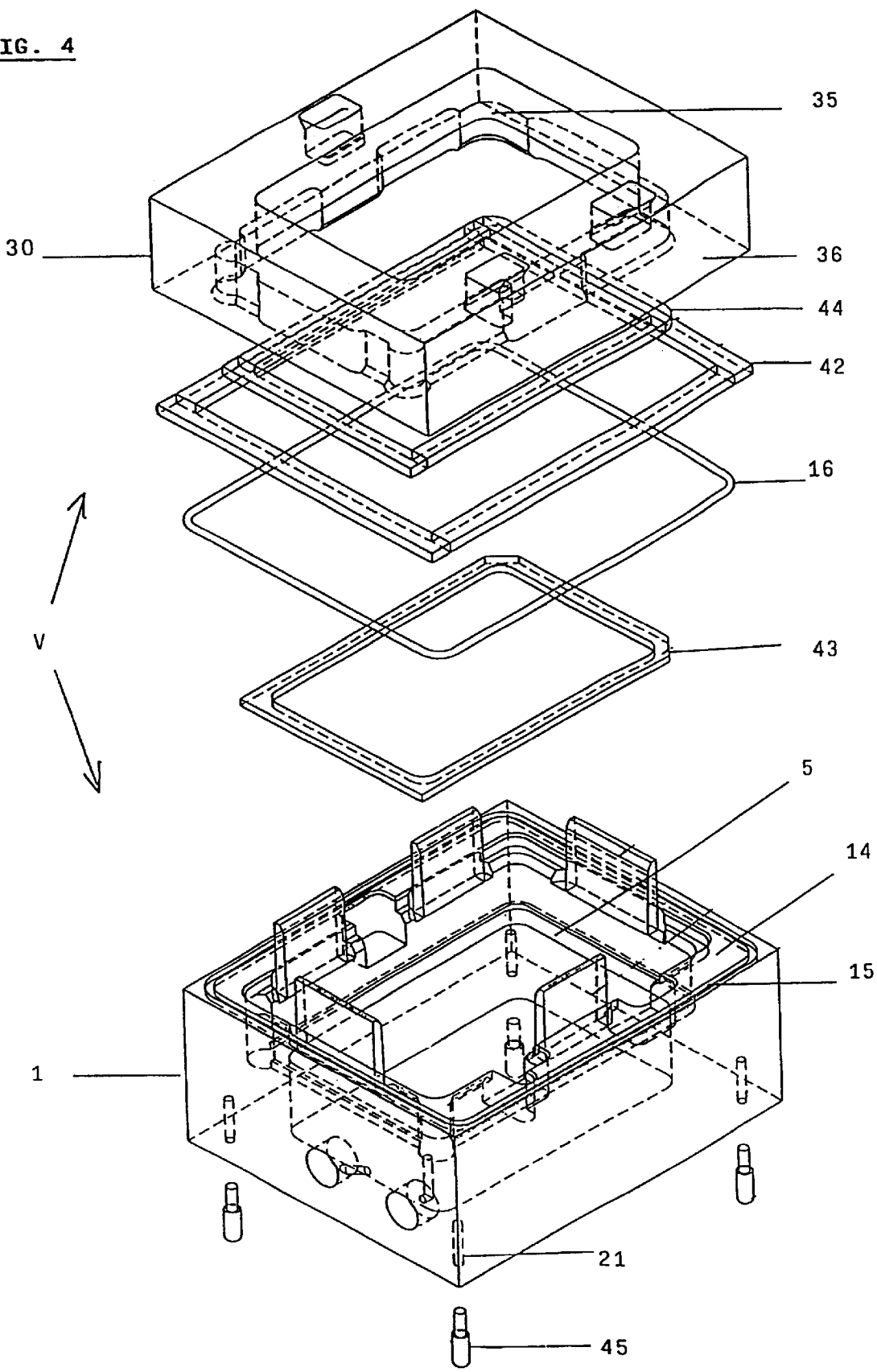
FIG. 4 shows an exploded view of the vacuum chamber according to the invention.

FIG. 4 shows an exploded view of the vacuum chamber V consisting of the lower part 1 and the cover 30, the lower part 1 and the cover 30 being sealed with respect to one another by means of a seal 16 which rests in the groove 15. The seal 16 does not press directly against the sealing surface 36 of the cover 30, but instead there is located between them a peripheral sealing strip 42 having a hardness of 30 Shore. A seal 43, which seals the lower filter support (not shown) with respect to the ledge 5 of the lower part 1, rests loosely on the ledge 5. The seal 43 of the lower filter support F2 is preferably a rubber gasket having a hardness of 60 Shore. The upper filter support F1 is sealed with respect to the sealing surface 35 of the cover 30 by way of a sealing strip 44. The hardness of the seal 44 is about 20 Shore.

Also shown are bolts 45 with which the vacuum chamber V is fixed in position by means of the bores 21.

Figure 5:
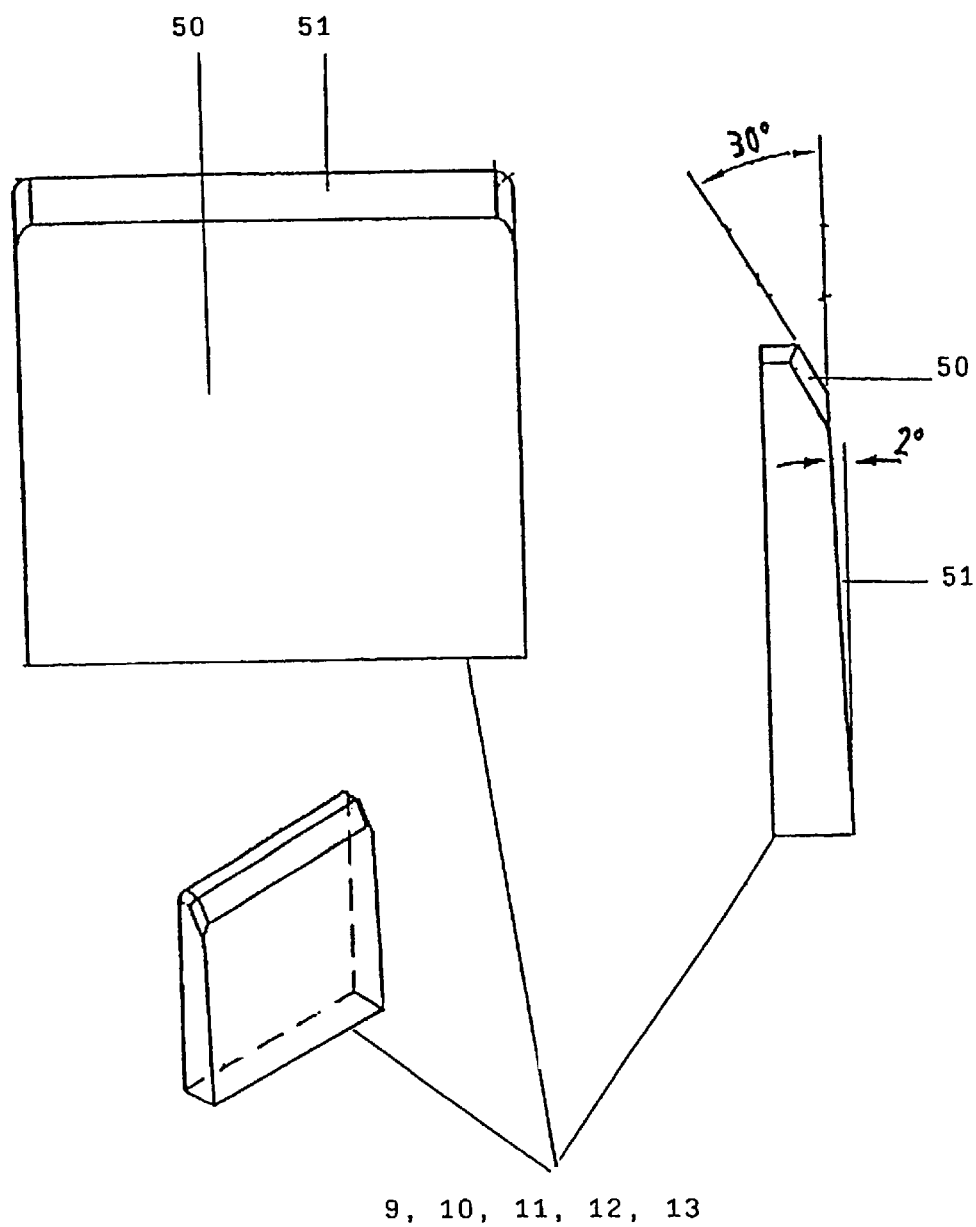
FIG. 5 shows a centring tab used in the vacuum chamber.

FIG. 5 shows a plan view, a side view and a perspective view of a guide tab 9 to 13 used for centring. It will be seen that the guide tab 9 has two bevels 50, 51 which differ from one another, the first bevel having an angle of about 30° and the second bevel having an angle of about from 0 to 5°, preferably 2°. The dimensional data in FIG. 5 are in mm and the size of a guide tab is 30×30×5 mm (height×width× thickness).

Figure 6:
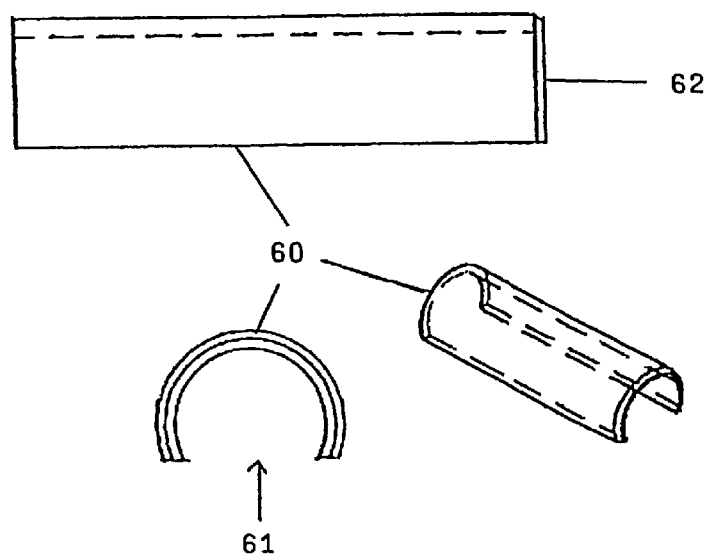
FIG. 6 shows a spacer sleeve in longitudinal view, cross-sectional view and side view.

FIG. 6 shows the spacer sleeves 60 for the filter holders F1, F2, which spacer sleeves 60 are pushed into the respective outer corner pipes of a filter support. The spacer sleeves 60 serve on the one hand to effect final alignment of the lower filter support F2 and to define a desired spacing between the upper filter support F1 and the lower filter support in order to create the upper vacuum region VO between the filter supports for the purpose of sucking through the fluid from the upper filter support into the lower filter support. If the filter supports F1, F2 were simply to be placed one above the other in the vacuum chamber V it would be impossible to establish two separate vacuum regions in the chamber V. The outlet connections with outlet tips 82 of the filter pipes 83 of the upper filter support F1 fit tightly into the filter pipes 81 of the support F2 located below, so that a vacuum VO established in the intermediate region would not be able to suck out preparation fluid located in the pipes of the upper filter holder F1. It is therefore necessary to provide a sufficiently large gap, that is to say upper vacuum region VO, between the two filter supports, F1, F2. Furthermore, it is absolutely necessary for reasons of preparation technology to prevent any of the fluid dripping down from being sprayed into adjacent pipes of the lower filter system F2. Otherwise there would be cross-contamination of neighbouring samples, which would render the result of the preparation unusable. The spacing between the two filter supports F1, F2 is therefore such that the outlet tips 82 of the upper filter support F1 are located about 1.5 mm inside the filter elements 81 of the pieces of the lower filter support F2. In order to ensure that spacing and the definition of the first vacuum region, cylindrical spacer sleeves 60 of a defined radius are therefore placed into the corner pipes, the spacer sleeves 60 being milled open, that is to say provided with a broad longitudinal slot 61, so that the corner pipes also are acted upon sufficiently by the vacuum. In order to align the lower filter support F2, the end faces 62 of the spacer sleeves 60 are bevelled. In a preferred embodiment, the spacer sleeve 60 is 31.5 mm long and has an outer diameter of 11.4 mm, the height of the partially open cylinder being 7.8 mm. The internal diameter is fixed at 9.2 mm and the end-face bevel is 0.5 mm×45°. This 45° bevelled portion makes the first mechanical contact with the corresponding guides on the lower part 1. By virtue of the geometry of the spacer sleeves, the further downward movement of the gripper arm brings about the corrections necessary for the filter supports F1, F2 to be received exactly. For the purpose of easy handling in laboratory operation, the spacer sleeves 60 are made of a material that, on the one hand, has the flexible properties of spring clips but, on the other hand, has sufficient resistance to chemicals and sufficient rigidity, so that the spacer sleeves 60 can be placed resiliently onto the four corner pipes of the filter supports F1, F2. 1.5 mm thick sleeves 60 of plexiglass were therefore chosen. For industrial production they can be made economically from plexiglass tubes. The slot 61 necessary for positioning on the four corner pipes is sufficiently large not to impede the establishment of the vacuum in that area. The spacer sleeves can also be arranged fixedly on the filter supports, for example in an injection-moulding process or the like.

Figure 7:
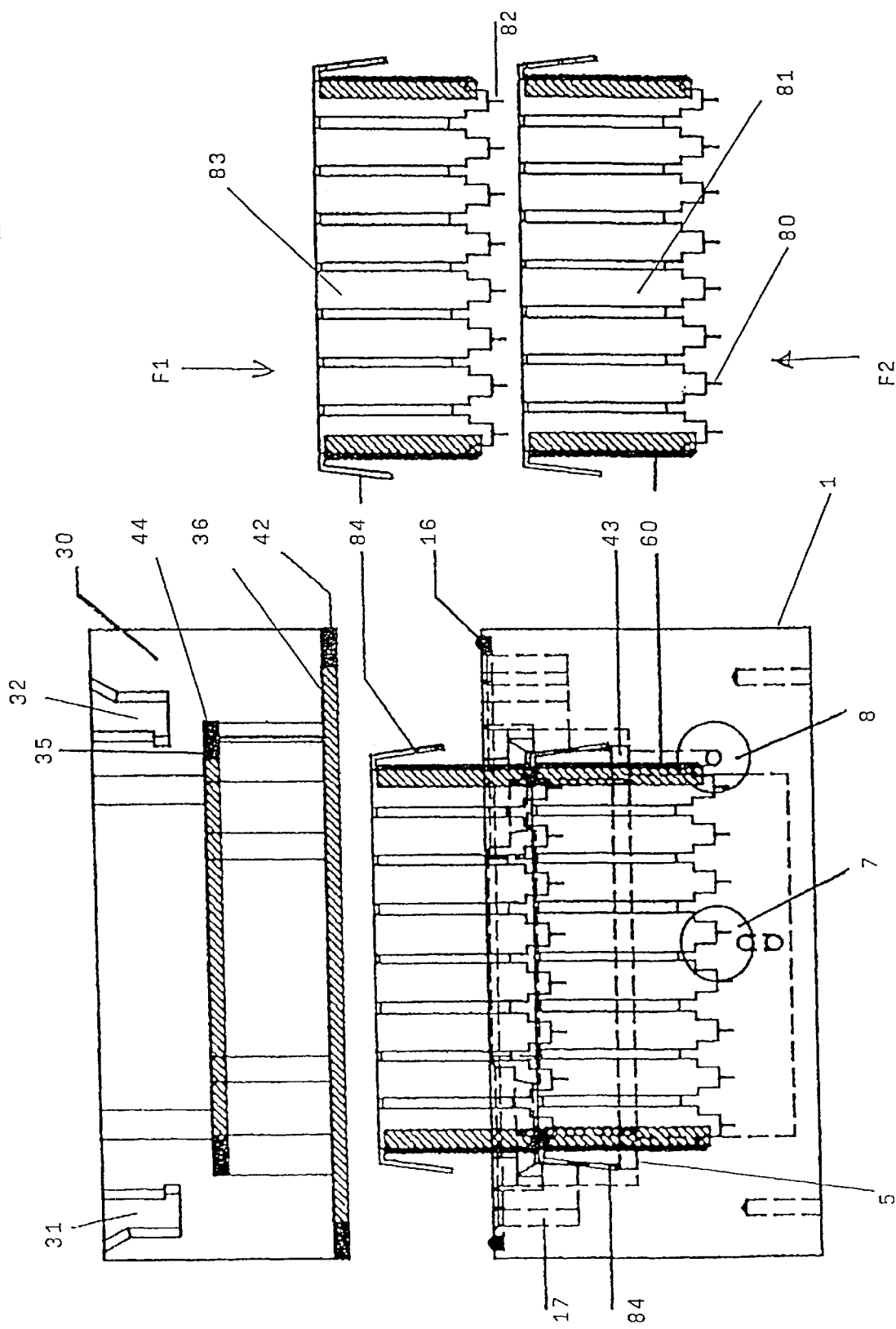
FIG. 7 shows a cross-sectional view of the vacuum chamber with the filter supports inserted and the cover not closed.

FIG. 7 shows the lower and upper filter supports, F1, F2 arranged one above the other in the lower part 1 of the vacuum chamber V, the outlet tips 80 of the individual filter elements 81, which here are constructed in the form of pipes, of the lower filter support F2 projecting into the lower vacuum region VU of the vacuum chamber V. The outlet tips 82 of the filter elements 83 of the upper filter support F2 project into the upper pipe region of the filter elements 81 of the lower filter supports F2. The upper vacuum region VO is defined by suitable selection of the spacer sleeves 60 that are positioned on the lower filter support F2. Also shown is the cover 30 before it is placed onto the lower part 1, the lower part 1 having in its sealing surface 14 a groove 15 with a rubber seal 16 which effects a seal with respect to the seal 42 of the sealing surface 36 of the upper part 30. The upper filter support F1 effects a seal with respect to the seal 44 of the upper part 30. In FIG. 7, the two filter supports F1 and F2 can again be seen at the side. The filter supports F1 and F2, which consist of the filter elements 81, 83, may be constructed in one piece. It is also possible, however, for a filter support F1, F2 to be constructed as it were in modular form, for example by assembling individual filter elements 81 or 83 by means of suitable connections. The filter supports F1, F2 also have side walls 84. The lower filter support F2 is seated on the seal 43 of the ledge 5 of the lower part 1 of the vacuum chamber and thus forms the lower vacuum region VU, which is vented or evacuated via the suction shaft 7. The upper vacuum VO is formed by the suction shaft 8. Furthermore, the grip recesses 31, 32 and 17 for the robot grippers are shown by way of example. The grip recesses 31, 32, 17 are open towards the top by way of a bevel in order to obtain better access for the robot. In their base region they have a groove so that the robot gripper can be braced in the recesses 31, 32, 17.

FIG. 8 shows the same situation as in FIG. 7 but now with the cover in place, and it will be seen that the upper filter support F1 is sealed with respect to the upper part 30 by the sealing surface 35 and a corresponding 44. Shown on the right-hand side in the drawing are the filter supports F1, F2, which are arranged one above the other, the upper vacuum region VO being defined by means of the size of the spacer sleeve 60.

The insertion of the filter supports F1, F2, shown diagrammatically in FIG. 1, into the vacuum chamber V and the components thereof in accordance with FIGS. 2 to 6 will be explained below with reference to FIGS. 7 and 8.

When the filter supports F1, F2 are being introduced from a pipetting robot PR (FIG. 10) into the vacuum chamber V by means of a gripping robot GR (FIG. 10), slight changes in position may arise in the course of their travel. If these changes are not eliminated, then in a robot system having no sensory feedback, as is the case here, there would soon be a mechanical catastrophe. For that reason, an enforced mechanical alignment is carried out by the vacuum chamber V itself during insertion of the filter supports F1, F2.

When the filter F2 that collects the fluid (lower filter) is inserted into the vacuum chamber V, it is the guide tabs 9 to 13 that make the first mechanical contact with the lower part 1 of the vacuum chamber V. Because the filter support F2 may undergo slight changes in position in the course of travelling from the pipetting station PR to the vacuum chamber V, the guide tabs 9, 10, 11, 12, 13 serve to bring the filter support F2 back into the required position during its insertion into the lower part 1 of the chamber V. The CRS 465 (gripping robot GR) used in this preferred embodiment can travel towards predetermined co-ordinates only by means of a "spline function" calculated in the C500 controller. For that reason it is necessary always to specify movement sequences that are not stringent in respect of the spline function. The robot gripper arm with the filter support F2 therefore initially approaches at moderate speed an approach position approximately 1 cm vertically above the final point of contact with the guide tabs 9 to 13. As the filter support F2 is slowly lowered, contact will be made with the bevels 50, 51 of the guide tabs 9 to 13, misplacements being compensated for firstly on the 30° bevels 50 and subsequently on the 2° inclinations 51 of the surfaces aligned perpendicularly to the direction of movement via the enforced downward movement of the gripper arm. After about 1 cm, the filter support F2 if flanked by the five alignment faces that taper downwards at an angle of 2° in such a manner that misplacements in the horizontal region relative to the lower part 1 of the vacuum chamber 1 are compensated for in every case. It is only then that the vertical alignment of the filter support F2 on the centring shafts 22, 23 of the chamber is effected. On the four outer corner pipes of the filter support there are mounted spacer sleeves 60 which, in addition to their function of rendering the upper filter support F1 accessible to the vacuum in the upper region of the chamber V, here perform their second function, namely the vertical correction for misplacements of the lower filter support F2. For this purpose, likewise 30° bevels 62 are located both on the spacer sleeves 60 and on the centring shafts 22, 23 of the vacuum chamber lower part 1. After having travelled about 2 mm, the filter support F2 is positioned by the downward movement of the robot arm in the correct position inside the lower part 1 of the vacuum chamber V. At the same time the gripping tool passes into the grip recesses 17, 18, 19 of the lower part 1. Approximately 1 mm above its final deposition point, the filter support F2 is released by the gripper of the robot arm and thus comes to rest on the seal 43 which rests on the ledge 5 of the lower part 1.

When the upper filter support F1 is installed by means of the robot gripper arm, its centring is effected in a similar manner by way of the guide tabs 9 to 13. The spacer sleeves 60 align the upper filter support F1 parallel to the lower support F2 already located in the lower part 1. If, nevertheless, a misplacement of the upper filter holder F1 should occur, it will be compensated for by the special construction of the vacuum chamber upper part 30. When, from a special part position, the cover 30 of the vacuum chamber V is placed by the gripper of the gripping robot onto the vacuum chamber lower part 1, the cover 30 makes its first contact with the guide tabs 9 to 13 of the lower part 1. For that purpose, in addition to having their 30° inner bevels, the latter have also been given short 45° outer bevels. The cover 30 receives them in special recesses 37 to 41. The cover 30 is aligned using the recesses 37 to 41 by way of the downward movement of the gripper. After about 0.5 cm, the cover 30 has been mechanically aligned with the lower part 1 of the vacuum chamber V to such an extent that the second function of the upper part 30 can be carried out, namely the correction of an upper filter holder F1 which may have been misplaced. For that purpose, the cover 30 is provided with 30° bevels 34 on the corresponding contact zones. The width of the bevel 34 is derived from the possible misplacement of the filter holder F1. Because the tolerances by way of the guide tabs 9 to 13 may be a maximum of 0.5 mm, the bevel 34 on the cover is about 0.5 mm wide on each side. This ensures sufficient tolerance in receiving the filter support F1. As a result of the downward movement of the gripper, the filter holder F1 is, if necessary, moved positively into the suitable position by means of the bevels 34 of the cover 30.

The sealing of the assembled chamber V is effected in three places in total. The lowermost zone is sealed by a rubber gasket having a hardness of 60 Shore. The second zone is the join between the lower part 1 and the cover 30 of the vacuum chamber V. It is formed by a combination of an O-ring 16 (60 Shore) and a resilient (30 Shore) sealing strip 42. The third zones is sealed with respect to the inner cover region by the upper filter F1. The cover 30 therefore has two supporting surfaces 35, 36 which are provided for mounting the sealing material. For that purpose they are roughened during the manufacturing process.

Figure 9:
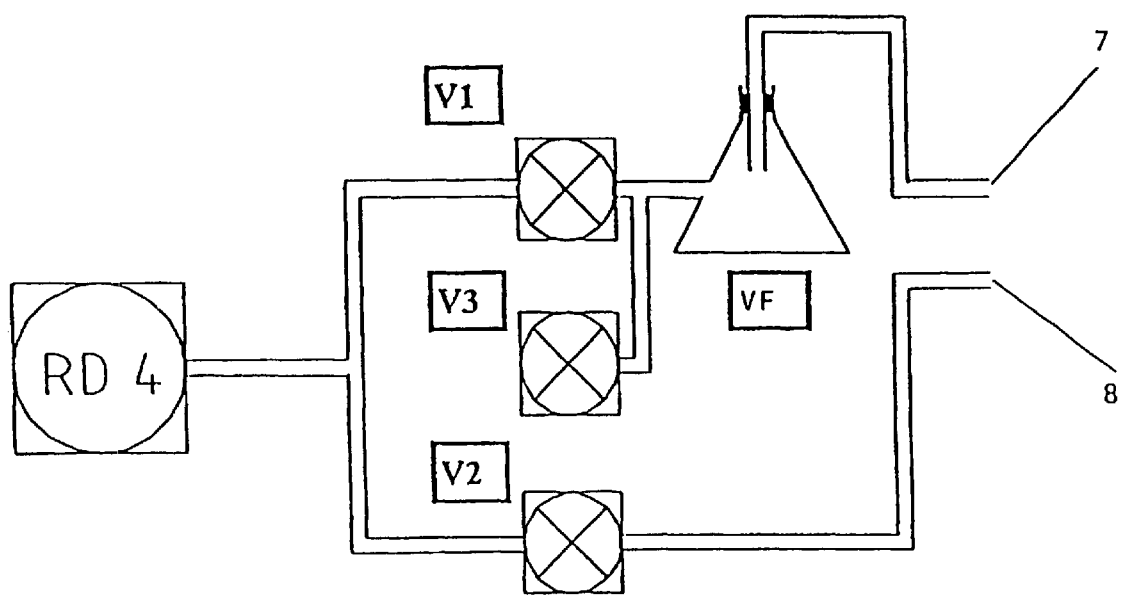
FIG. 9 shows a diagrammatic view of the valve system.

FIG. 9 shows the valve system necessary for operating the vacuum chamber. Starting from an oil pressure pump RD4, a vacuum hose is connected at a Y-connection to two electric valves V1, V2, which serve for the controlled establishment of two vacuum regions in the chamber V, namely the upper vacuum region VO between the two filter supports F1, F2 and the lower vacuum region VU for aspirating the fluid from the lower filter support F2. The valve V2, which is responsible for the upper vacuum region, is directly connected via a vacuum hose to the corresponding connection 8 of the chamber V. The other valve V1, which controls the evacuation of the base region, is connected via a vacuum hose to the vent pipe of a vacuum trap F. The lateral hose coupling of the trap F is connected by a hose connection to the connection 7 of the lower region of the vacuum chamber V. Using this arrangement, therefore, the water volume of about 500 ml can be removed from the system. Between the vacuum trap F and the controlling valve V1 there is connected by means of a T-piece a vent valve V3 which plays an important role in maintaining normal air pressure in the lower chamber region. The valve V3 makes a connection to normal air pressure.

The three potential valves V1, V2, V3 each have their own controlling electronics system which can be actuated by the control software via a decoding apparatus of a PC. The decoding apparatus likewise assumes the control of the oil pressure pump RD4, so that the control software is also able to control its activity. The valves V1, V2, V3 can be simple gas valves without special coatings. Their opening and closing behaviour can be altered by way of the controlling electronics system. For example, the two vacuum valves V1, V2, after receiving their actuation signal, open to the preset extent linearly over a period of 2 seconds. This delayed opening prevents the vacuum chamber from being evacuated too quickly by the connected oil pressure pump RD4. The control software first starts the oil pressure pump RD4 which then generates a partial vacuum in the entire region of supply to the valves V1, V2. After about 5 seconds, depending upon the requirements of the preparation step currently in progress, the control software sends the pulse for opening one of the two valves V1, V2. If that valve were to open too quickly, the resulting surge could damage the filter system or the vacuum chamber V. The vent valve V3, which is connected in parallel with the lower vacuum region of the chamber V, opens to its full extent linearly over a period of 0.1 second. It is then activated by the control software at predetermined time intervals when the upper region of the vacuum chamber V is to be evacuated, but the lower it to have normal air pressure. This is the preparation step in which fluid is sucked from the pipes of the upper filter support F1 into the lower filter support F2. Here a creeping partial vacuum must be removed from the system as quickly and effectively as possible. Because is can be assumed that in this case the pressure difference is small, the valve V3 is rapidly opened or closed to its full extent. A partial vacuum possibly building up in the base region of the chamber V is kept negligibly small by frequent venting in this manner.

During the plasmid preparation a waste volume of about 500 ml is formed and must be conveyed out of the lower region of the chamber V. The waste consists of the chemicals necessary for the preparation and the cell residues of the bacteria. The fluid therefore cannot be regarded as harmless from both its chemical and its biological nature and so it must be stored intermediately in a suitably secured container in order that it can be disposed of in a controlled manner when the preparation work is complete. The vacuum chamber V has therefore been provided in its lower region with a suction site 7 which is connected via a removal line system to the vacuum trap VF. The vacuum present in the lower region during the preparation ensures that any fluid arising from the lower filter support F2 is immediately sucked into the vacuum trap VF, which at the same time acts as an intermediate store. The control valve V1, which is responsible for the lower vacuum, is equipped with a brass closure without special protective washers for reasons of cost. Because of the aggressive nature of the preparation fluids this control valve V1 is arranged upstream of the vacuum trap VF. It is therefore also possible to select a vacuum trap VF of economical material (pressed glass). An oil pressure pump (model RD4, Vakubrand) having a suction power of 4.3 m$^3$/h is used to generate the vacuum. If the oil pressure pump is activated, the vacuum builds up upstream of the valve V1 but not in the vacuum trap VF, which is under normal air pressure until the valve V1, which is actuated by way of the electronic control means, is opened. The control means is so designed that the valve V1 opens proportionally over a period of 1 second, so that the vacuum does not build up so rapidly in the trap VF. The vacuum load on the trap VF therefore exists only during the period in which the preparation fluids are being moved through the filter materials. Because during that period the weakest point of the system is the 0.7 mm thick plastics dish of the filter support F1, which is directly connected to normal air pressure, there is no risk of the vacuum trap's imploding at any time during the preparation operation. Even if there should be a blockage of the filter material in all the pipes of the filter support F1, F2, the vacuum chamber V is so constructed that the lower rubber seal 43 acts as a safety valve. The rubber seal 43 will be drawn out of its lateral bevel into the chamber V and by means of the opening so produced the vacuum will return to normal air pressure. Destruction of the filter support F2 is therefore also ruled out. In order that the fluid to be sucked out is removed as quickly as possible from the lower chamber region, the suction opening 7 has been mounted directly on the base of the chamber V. The opening is connected directly to the suction connection 7 via a bore.

In order to be able to compensate for slight material tolerances of the filters F1, F2 and to achieve secure closure of the vacuum chamber V, the materials of the three seals have the following properties:

The sealing material of the lower chamber part 1 must be a material of moderate rigidity, in the present case the hardness is 60 Shore. This ensures that during the cyclic breaking of the creeping vacuum from the upper chamber regions, the seal of the upper filter support F1 with respect to the cover 30 is not broken.

The sealing material of the cover 30 must be very soft and resilient (20 Shore). This ensures sufficient sealing of the cover 30 with respect to the upper filter support F1 and with respect to the O-ring 16 of the lower chamber half 1. By virtue of its very resilient nature it is also possible to compensate for manufacturing tolerances of the filter support F1. The manufacturing tolerances of the filter supports F1, F2 have a two-fold effect: on the one hand they affect the supporting height of the lower filter support F2 and on the other hand they also affect the sealing of the upper filter support F1 with respect to the cover 30.

The O-ring 16 of the lower part 1 seals the chamber V with respect to the very soft sealing material 42 of the cover 30. The O-ring 16 has a diameter of 2 mm. As a result of its small supporting surface, a considerably smaller contact pressure of the cover 30 against the lower part 1 of the vacuum chamber V is necessary to provide an adequate seal. For example, the weight of the cover 30 together with the vacuum being built up in the interior of the chamber V is sufficient to close the cover 30 tightly with the filter supports F1, F2 it encloses. That point is very important for an unsupervised preparation carried out by a robot system because a vacuum that does not build up correctly will bring about the disruption of the entire plasmid preparation.

Furthermore, it is necessary to rely on directed aspiration of the fluid from the upper filter elements 83 into the filter supports or collecting container F2 arranged below. The fluid must remain in the lower filter support F2 without being immediately sucked through into the base region of the chamber V. When the vacuum develops in the upper region of the chamber V, then at the point at which fluid has not yet dripped into the lower filter support F2, a small amount of gas will rise upwards through the unwetted filter support F2. A slight vacuum will therefore be formed in the lower region of the chamber V. Once all the fluid has changed from the upper filter support F1 to the lower filter support, normal atmospheric pressure will become established in the cover region of the vacuum chamber V. As a result, the partial vacuum initially formed in the base region of the chamber V will suck through some of the fluid then located in the lower filter support F2 onto the base of the chamber V. In order to avoid this effect, the vent valve V3 is opened at intervals by the software control means. At the beginning of the venting process, full opening of the vent valve V3 takes place after every second, then after about 10 seconds for every 5 seconds that have elapsed, the opening speed of the valve V3 being at its maximum. For safety reasons, this cyclic venting of the lower vacuum region VU is kept constant while the upper vacuum region VO is connected to the vacuum. In the case of unsupervised robot preparations, a leakage in the lower region of the chamber V could result in a constant build-up of a partial vacuum. This can be compensated for by the cyclic ventilation of the lower region of the chamber V.

Figure 10:
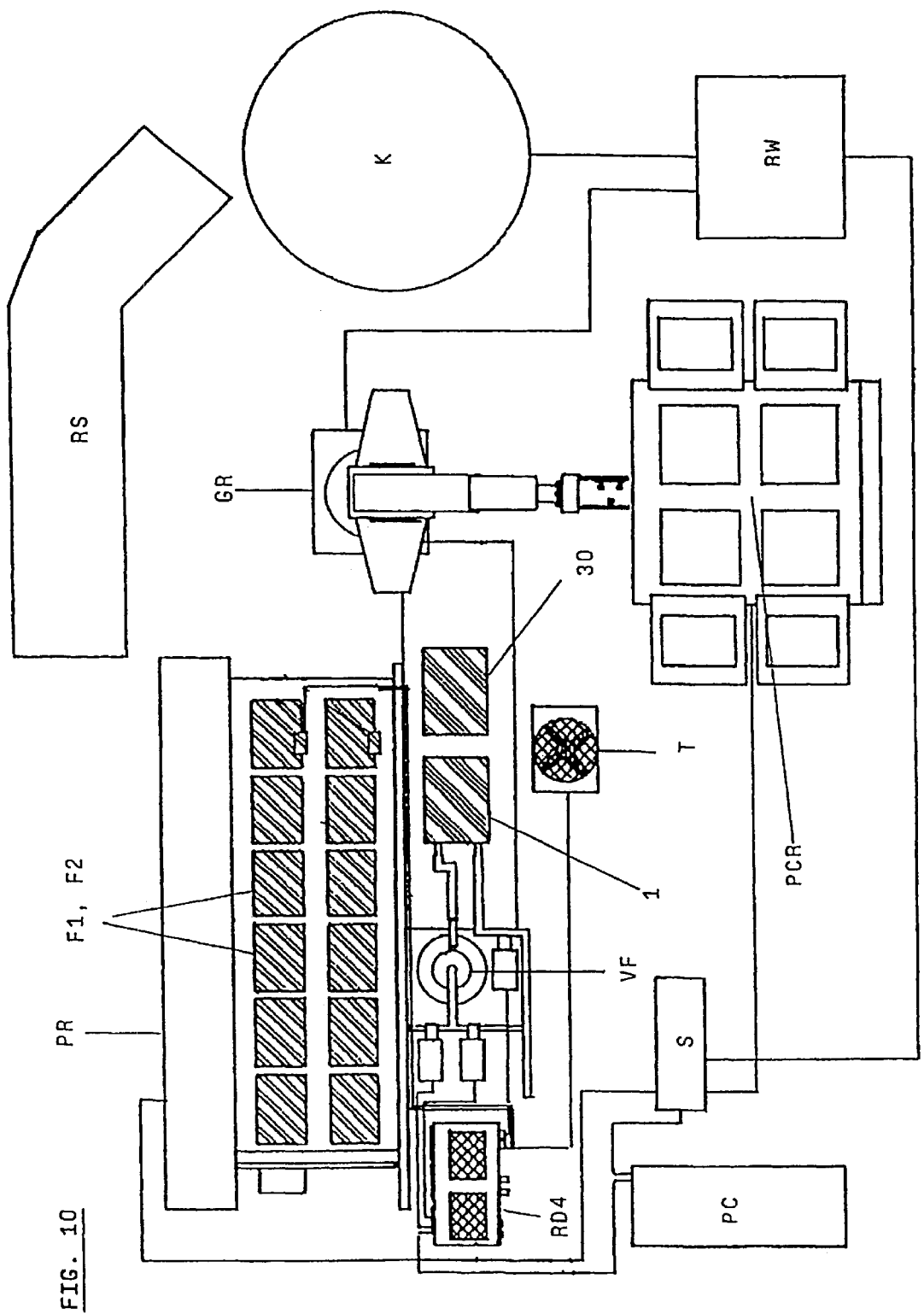
FIG. 10 shows a diagrammatic view of the entire apparatus for automatic plasmid preparation.

FIG. 10 shows a diagrammatic representation of the entire system for automatic plasmid preparation. The system comprises a pipetting robot PR (BIOMEK 2000), the vacuum system having the pump RD4, the valves V1, V2, V3, the vacuum trap VF and the vacuum chamber V, a gripping robot GR (CRS 465), a PCR machine (PTC 225, MJ-Research), a fixed shelving system RS for critical laboratory equipment (high salt buffer, acids etc.) and a carousel K (i.e. a rotatable shelving system for laboratory equipment). The system also comprise a dryer T for the filter supports F1, F2. For controlling the gripping robot GR, the latter is connected to a Risc-Workstation RS (C500) which is operated by way of a serial interface S (preferably an RS 232 interface) by a PC control computer PC which monitors the entire automatic plasmid preparation sequence. The arrangement of the gripping robot GR is such that it has access to the filter supports F1, F2 arranged on the pipetting robot PR, to the vacuum chamber V consisting of lower part 1 and cover 30, to the two shelving systems RS, K, to the dryer T and to the PCR machine PCR. The cover 30 of the vacuum chamber V has its own deposition site. The preparation sequence of the gripping robot GR, which is equipped with a three-fingered hand, is as follows in accordance with the Qiagen protocol: the gripping robot GR takes a filter support F2 for the lower filter from the carousel K and inserts it into the lower part 1 of the vacuum chamber V. It then takes from the pipetting robot PR the upper filter support F1, the pipes (filter elements 83) of which have been pipetted with the appropriate preparation fluid by the pipetting robot PR, and places it onto the lower filter F2 in the lower part 1 of the vacuum chamber V. The vacuum chamber cover 30 is then put in place and the filtration, that is to say the transport of the fluid through the filter supports F1, F2, is carried out by applying a suitable vacuum to the upper or lower vacuum region. When the filtration is complete, the vacuum chamber V is opened automatically by the gripping robot GR and the uppermost filter F1 is removed and disposed of. The lower filter support F2 is again conveyed into the pipetting robot PR and filled with the appropriate preparation fluid, while the gripping robot GR takes from the carousel K a further filter support F2 to be used as lower filter support for the next filtration step and introduces it as lower filter support F2 into the lower part 1 of the vacuum chamber V. The pipetted filter support is then taken from the pipetting robot PR and inserted as upper filter F1 into the lower part 1 and the vacuum chamber V is closed. When the transport of fluid is complete, the chamber V is opened again, the upper filter support F1 is disposed of and the lower filter support F2 is again conveyed into the pipetting robot PR for the introduction of the next preparation fluid. If the next filtration step is the last, the gripping robot GR takes a collector support from the carousel and inserts it as lower support F2 into the lower part 1. The appropriate pipetted filter support is then taken from the pipetting robot PR and introduced as upper filter support F1 into the lower part 1 and the vacuum chamber V is closed. In what is then the third filter step, the preparation fluid containing pure DNA is sucked into the collector support F2, and the filtration in accordance with the Qiagen protocol is complete.

In order to control the entire system it is necessary to have a special control system and regulation means for each of the units. In other words, each of the modules of the entire system is provided with its own control software. All the control operations are regulated within the control software and do not require feedback to the commanding system. Windows NT is preferably selected as the operating system, because it has stable pre-emptive multitasking which also supports phase-parallel sub-programs and it is possible to use interprocess communication methods.

Figure 11:
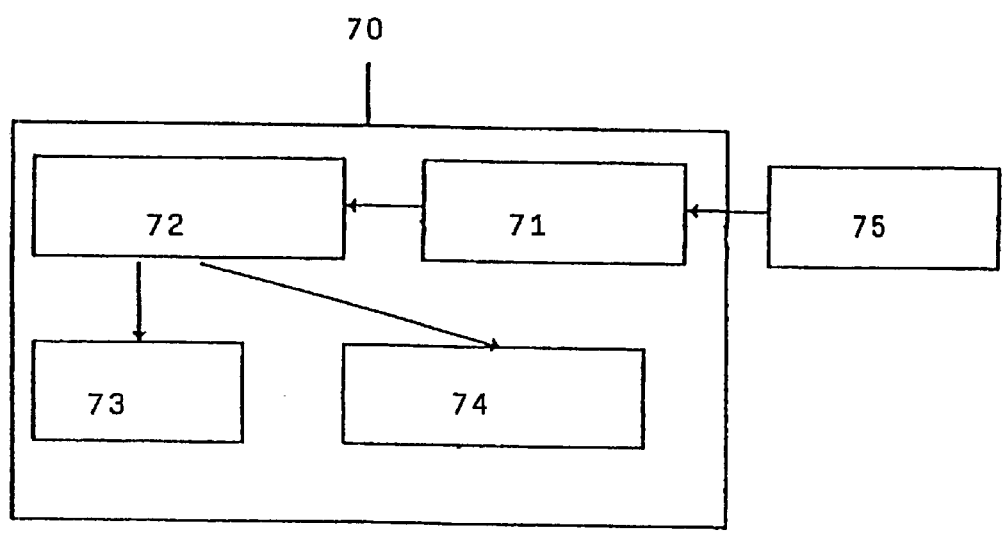
FIG. 11 shows a diagrammatic view of the vacuum chamber electronic module.

Finally, FIG. 11 is a block diagram showing the actuation of the module 70 of the vacuum chamber V. The module 70 comprises the sub-modules "control vacuum chamber" 71, "electronics system" 72, "valves" 73 and "oil pump RD4" 74, the module 70 being controlled by the module "commanding robot" 75, that is to say starts the actuation of the vacuum chamber. In the module 70, three valves V1, V2, V3 and an oil pressure suction pump RD4 are controlled by a computer PC. The valves V1, V2, V3 that are used are connected in the interactive state, since the closing member thereof in the interior of the valve is pressed against the valve seal by a spring.

List of Reference Numerals 1-lower part
2-inner chamber lower part
3-lower portion
4-upper portion
5-ledge
6-groove
7-suction shaft
8-suction shaft
9-guide tab
10-guide tab
11-guide tab
12-guide tab
13-guide tab
14-sealing surface lower part
15-groove
16-rubber seal
17-grip recess
18-grip recess
19-grip recess
20-bevelled guide edge lower part
21-bore
22-centring shaft
23-centring shaft
30-cover
31-grip recess
32-grip recess
33-grip recess
34-bevelled guide edge cover
35-ledge cover (sealing surface of the upper filter support)
36-sealing surface cover/lower part
37-recess
38-recess
39-recess
40-recess
41-recess
42-seal cover/lower part
43-seal lower support
44-seal upper support
45-bolt
50-bevel guide tab
51-bevel guide tab
60-spacer sleeve
61-slot
62-bevelled end edge
70-module "vacuum chamber"
71-module "control vacuum chamber"
72-module "electronics system"
73-module "valves"
74-module "RD4 oil pump"
75-module "commanding robot"
80-outlet tip
81-filter element
82-outlet tip
83-filter element
84-side wall filter support
V-vacuum chamber
VO-upper vacuum region
VU-lower vacuum region
F1-upper filter support
F2-lower filter support
V1-valve
V2-valve
V3-valve
VF-vacuum trap
RD4-oil pump
PR-pipetting robot
RS-shelving system
K-carousel
GR-gripping robot
RW-Risc-Workstation
T-dryer unit
S-interface
PC-control computer

What is claimed is:

1. A vacuum system for the directed transport of a substance, having a vacuum chamber (V) which comprises a first permeable means (F1) and a second permeable means (F2), which are arranged one above the other, and two vacuum regions (VO, VU) an upper vacuum region (VO) being defines by a space between the first permeable means (F1) and the second permeable means (F2) and a lower vacuum region (VU) being defined by a space between the second permeable means (F2) and a base of the vacuum chamber, a vacuum pump RD4), a first electronically controlled valve (V1) for the lower vacuum region (VU), a second electronically controlled valve (V2) for the upper vacuum region (VO), and a vacuum trap (VF) arranged at the lower vacuum region (VU) for receiving a waste volume, a third valve (V3), arranged upstream of the first electronic valve (V1), for breaking a creeping vacuum in the loser vacuum region (VU), wherein:

vacuum is generated and established in each of the upper and the lower vacuum regions (VO, VU) independently of one another so that a substance is transported in two steps through the first permeable means (F1) and the second permeable means (F2) into the lower vacuum region (VO).

2. The vacuum system according to claim 1, wherein the vacuum system has only two vacuum regions (VO, VU).

3. The vacuum system according to claim 1, wherein the first permeable means (F1) is formed by a filter support.

4. The vacuum system according to claim 3, wherein the second permeable means (F2) is formed by a filter support.

5. The vacuum system according to claim 1, wherein the vacuum system has a cover (30) and a lower part (1).

6. The vacuum system according to claim 5 wherein the lower part (1) of the vacuum chamber (V) has a ledge (5) for supporting the second permeable means (F2).

7. The vacuum system according to claim 5 the lower part includes side walls which are provided in the side walls of the lower part (1) of the vacuum chamber (V) recesses (17, 18, 19) for a gripper of a robot (GR).

8. The vacuum system according to claim 7, wherein the lower part (1) of the vacuum chamber (V) has guide tabs (9, 10, 11, 12, 13) having correcting levels (50, 51) for the insertion of the first permeable means (F1) and the second permeable means (F2) into the lower part (1).

9. The vacuum according to claim 8, wherein the guide tabs (9, 10, 11, 12, 13) have a first and second bevel angle (50, 51).

10. The vacuum system according to claim 9, wherein the first bevel angle (50) is about 30° and the second bevel angle (51) is about 2°.

11. The vacuum system according to claim 5, wherein the lower part (1) has a beveled peripheral guide edge (2), with which the first and second permeable means (F1, F2) come into contact on insertion into the lower part (1) of the vacuum chamber (V).

12. The vacuum system according to claim 5, wherein the cover (30) of the vacuum chamber (V) has a beveled guide edge (34), which comes into contact with the first permeable means (F1) when the cover (30), is put in place on the lower part (1).

13. The vacuum system according to claim 12, wherein the bevel guide edge is at an angle of 30°.

14. The vacuum system according to claim 5, wherein the cover (30) has wall region recesses (31, 32, 33) for a gripper of a robot (GR).

15. The vacuum system according to claim 5, wherein the cover (30) has a supporting surface (35) for sealing the upper filter support (F1).

16. The vacuum system according to claim 15, wherein the sealing materials for the supporting surface sealing the upper filter support (F1) has a hardness of 20 Shore.

17. The vacuum system according to claim 16, wherein a joint between the cover (30) and the lower part (1) is formed by a combination of an O-ring (16) and a non-resilient sealing strip (42), the O-ring (16) providing a seal of 60 Shore and the sealing strip (42) of 30 Shore.

18. The vacuum system according to claim 17, wherein the lower filter support (F2) sealing is effected by a seal (43) having a hardness of 60 Shore.

19. The vacuum system according to claim 8, wherein the cover (30) has corresponding receiving means (37, 38, 39, 40, 41) for receiving the guide tabs.

20. The vacuum system according to claim 1, wherein the upper filter support (F1) has a number N of pipe-shaped filter elements that are connected to form a filter support.

21. The vacuum system according to claim 20, wherein the lower filter support (F2) has N pipe-shaped filter elements that correspond to the filter elements (81, 83) of the upper filter support (F1) and are connected to form a filter support.

22. The vacuum system according to claim 21, wherein there are mounted four corner pipes of the two filter supports (F1, F2) and a spacer sleeve (60) which, in addition to its function of defining the spacing between the two filter supports (F1, F2), also effects a vertical correction of misplacements of the lower support (F2) by engaging in centering shafts (22, 23) in the lower part (1) of the vacuum chamber (V).

23. The vacuum system according to claim 22, wherein the spacer sleeves (60) are cylindrical in shape, having a through slot (61) in the axial direction so that vacuum is able to act on the corner pipes.

24. The vacuum system according to claim 23, wherein the spacer sleeves (60) have code end faces which are beveled.

25. The vacuum system according to claim 22, wherein the length of the spacer sleeves (60) is such that outlet tips (82) of the upper filter support (F1) are located inside the pipes (81) of the lower filter support (F2).

26. The vacuum system according to claim 25, wherein the outlet tips (82) of the upper filter support (F1) are located 1.5 mm inside the pipes (81) of the lower support (F2).

27. The vacuum system according to claim 22, wherein the spacer sleeves (60) are made of plexiglass.

28. The vacuum system according to claim 1, wherein the vacuum chamber (V) is manufactured from plexiglass, glass or special steel of a suitable thickness.

29. The vacuum system according to claim 28, wherein the vacuum chamber (V) is manufactured by an injection-moulding process or by a milling process.

30. The vacuum system according to claim 1, wherein the lower part (1) of the vacuum chamber (V) has a suction shaft (7) for the lower vacuum region (VU) and a suction shaft (8) for the upper vacuum region (VO).

31. The vacuum system according to claim 1, wherein each valve (V1, V2, V3) has its own controlling electronics system which can be actuated by the control software via a decoding apparatus of a PC.

32. The vacuum system according to claim 1, wherein a dry unit (T) for drying the filter supports (F1, F2) is also provided.

33. The vacuum system according to claim 1 further comprising means for transporting a substance through at least one permeable means (F1) to the second permeable means (F2).

* * * * *